(12) United States Patent
Cordry (10) Patent No.: US 9,726,013 B2
(45) Date of Patent: Aug. 8, 2017

(54) NO PURGE SAMPLER (71) Applicant: Kent Cordry, Las Cruces, NM (US)

(72) Inventor: Kent Cordry, Las Cruces, NM (US)

(*) Notice: Subject to any disclaimer, the term of this patent is extended or adjusted under 35 U.S.C. 154(b) by 257 days.

(21) Appl. No.: 14/528,252

(22) Filed: Oct. 30, 2014

(65) Prior Publication Data
US 2016/0123142 A1 May 5, 2016

(51) Int. Cl.
*E21B 49/00* (2006.01)
*E21B 49/08* (2006.01)
*G01N 1/12* (2006.01)

(52) U.S. Cl.
CPC .............. *E21B 49/082* (2013.01); *G01N 1/12* (2013.01)

(58) Field of Classification Search
USPC .......................... 73/152.23, 152.26, 152.18
See application file for complete search history.

(56) References Cited

U.S. PATENT DOCUMENTS

| | | | | |
|---|---|---|---|---|
| 2,623,594 A * | 12/1952 | Sewell | ............... | E21B 33/1243 166/100 |
| 4,050,315 A | 9/1977 | Markfelt | | |
| 4,157,664 A | 6/1979 | Robinson | | |
| 4,254,830 A | 3/1981 | Garney et al. | | |
| 4,266,429 A | 5/1981 | Brovold | | |
| 4,271,704 A | 6/1981 | Peters | | |
| 5,454,275 A | 10/1995 | Kabis | | |
| 5,507,194 A | 4/1996 | Scavuzzo et al. | | |
| 5,753,831 A | 5/1998 | Mohs | | |
| 5,878,813 A | 3/1999 | Ridgeway, Jr. | | |
| 5,902,940 A * | 5/1999 | Stern | ........................ | G01N 1/12 294/68.22 |
| 6,167,962 B1 | 1/2001 | Pratt | | |
| 6,196,074 B1 | 3/2001 | Varhol | | |
| 6,837,120 B2 * | 1/2005 | Cordry | ..................... | G01N 1/12 73/864.63 |

FOREIGN PATENT DOCUMENTS

JP 8-220084 A 8/1996

OTHER PUBLICATIONS

Alexander, A. W. et al., "Field Trial of a New Commercially Available Diffusive Ground-Water Sampler," Bunnell-Lammons Engineering, Inc. Greensville, South Carolina, 6 pages.
Eon Products, Inc., Lithonia, Georgia, "EON Groundwater Diffusion Sampler," brochure, 2 pages.

(Continued)

*Primary Examiner* — Clayton E LaBalle
*Assistant Examiner* — Warren K Fenwick (57) ABSTRACT

A no purge sampler for collecting fluid samples includes a flexible tube having a sealed first end and a second end, the tube defining an interior cavity, a check valve disposed at the second end of the tube, and at least one aperture above the check valve. To collect fluid samples, the no purge sampler is lowered into the fluid to be sampled. The at least one aperture streamlines the tube as it is lowered into the fluid reducing drag-down and mixing. Once the sampler reaches the desired depth, the sampler is pulled upwards allowing fluid to enter the interior cavity. The sampler is then pulled out of the fluid without losing any of the fluid in the interior cavity of the tube or contaminating the sample with any extraneous fluid.

4 Claims, 12 Drawing Sheets

(56) References Cited

OTHER PUBLICATIONS

Eon Products, Inc., Lithonia, Georgia, "EON Diffusion Sampler," brochure, 1 page.
Horton, P. D. et al., "The California Groundwater Purging Study for Petroleum Hydrocarbons," Proceedings of the Eleventh National Outdoor Action$^{SM}$ Conference and Exposition, Las Vegas, Nevada, Apr. 1-3, 1997, pp. 109-122.
QED GroundWater Specialist, "Micro Purge," brochure, pp. 3-5.
Vroblesky, D. A. et al., "Diffusion Samplers as an inexpensive Approach to Monitoring VOCs in Ground Water," GWMR (1997) Summer, pp. 177-184.

\* cited by examiner

NO PURGE SAMPLER

FIELD OF THE INVENTION

This invention generally relates to sampling devices used for sampling water in a groundwater well and collecting an unaltered water sample from a specific water strata. More particularly, the invention relates to a disposable grab sampler that eliminates the need for purging, reduces or eliminates mixing and drag-down, and provides a representative sample of groundwater from monitoring wells during the sampling process.

BACKGROUND

The conventional practice of purging water during the process of sampling water found in a groundwater monitoring well is based on the need to remove stagnant water from the portion of the well that is not open to the water bearing formation prior to sampling. It is thought that this stagnant water is not representative of the in-situ water quality and, therefore, must be removed before any type of accurate sampling process can be allowed to proceed. Traditional practices of bailing or high-rate pumping of water from a well during the purging process necessitate the removal of multiple "well volumes" to ensure adequate removal of all stagnant water from the sampling zone. For instance, in a known procedure for sampling ground water monitoring wells, three to five times the volume of the standing water in a well screen, casing, and surrounding filter pack is removed prior to collecting a sample to assure that only unaltered formation water is tested.

The use of traditional sampling devices and pumping systems to conduct groundwater monitoring results in a time consuming and costly sampling process. The use of samplers, such as bailers, portable pumps, and high-speed pumps mixes the stagnant water in the well casing with the "fresh" water in the screened interval. Moreover, high-rate pumping of water from the well can induce drag-down within the well and surrounding formation, causing stagnant water to be mixed with incoming water and contaminating the samples. High-volume purging often requires hours to complete, and results in the creation of tens or hundreds of gallons of purge water, often must be contained for disposal as a liquid hazardous waste.

The cost of properly disposing of groundwater that qualifies as a hazardous material further adds to the cost of the sampling process. It is therefore desirable to minimize the amount of water that is required to be removed prior to collecting the water sample, yet still provide a representative sample.

Several methods have been proposed to deal with this specific problem, One of the methods that has been gaining acceptance in the groundwater monitoring community is the "low flow" sampling process. Low flow sampling is the process of pumping a monitoring well at a very low flow rate before sampling to eliminate the mixing of stagnant water above the screened interval with the fresh water in the screened interval. During low flow sampling, a very limited volume of water is removed from the well, resulting in minimal drawdown of the water column within the well. Low flow sampling is based on the rationale that a screened section of a well casing has fresh formation water flowing through it at a rate equal to the rate it moves through the aquifer. Water in a non-screened section of the well casing, above the screened section, is stagnant and thus not representative of in-situ well water conditions. Low flow sampling focuses on removing water only from the screened interval.

The low flow sampling process requires that a dedicated pump be left in the well for sampling purposes. The pump is lowered into the well and is positioned in the screened section of the well. As the pump is lowered downwardly through the well, it first passes through the stagnant water existing in the non-screened section of the well casing. As it is lowered, it mixes the stagnant water with the fresh formation water in the screened zone of the well below. Because of this initial mixing, the pump must sit undisturbed within the screened section of the well until the well once again reaches equilibrium. After equilibrium is reached, usually in a matter of days, sampling can begin. The pump is started and water is withdrawn from the well at a rate which does not result in draw down of the water level and mixing of the stagnant water into the well screened section. As the water is slowly pumped from the well, it is monitored for the stabilization of indicator parameters. As soon as the parameters are stabilized, indicating that the pumping system has been purged of extraneous water and that the withdrawn water is coming from the formation, a sample is collected.

The disadvantages of the low flow sampling process are that it is often slow and complex and requires specialized training of the sampling personnel. Moreover, the capital costs associated with the equipment used to conduct low flow sampling are high. The dedicated pump and tubing are costly and additional surface instrumentation further adds to the cost of the procedure. Accordingly, there is a need for a sampling device that is quick and easy to use that does not require extensive training of the field personnel. Moreover, it is desirable to have a sampling device that does not require costly equipment to operate.

Another known sampling method that has been proposed is the "no purge" sampling method that is carried out by using a conventional sampler. Like the low flow sampling method, the no purge concept is based on the premise that a well's intake screen and filter pack are more permeable than the formation being sampled, and that because of this, water is constantly flowing through the well's screened section. If there is no stagnant water in the well casing, as when the top of the screened section is positioned above the top of the water table, it is proposed that purging is not needed. A conventional bailer is dropped into the water column and a sample of groundwater is immediately collected. To successfully use this procedure, however, the screened section of the well casing must extend above the water table, thereby eliminating the presence of stagnant water that could mix with the formation water as the bailer is lowered. The absence of such stagnant water eliminates the prospect of the recovered bailed water sample becoming contaminated.

Another sampling method is "diffusion" sampling. Diffusion sampling is a passive sampling process that is conducted by using a sealed polyethylene bag filled with water that is lowered into the screened section of a monitoring well. Molecular diffusion of volatile organic contaminants (VOC's) causes chemical equilibrium to occur between the water in the sampler and the water in the well. After allowing approximately 14 days for the concentrations to equilibrate, the sampler is withdrawn and the water in the bag is removed and analyzed, This method has limited applicability, however, as only specific types of contaminants diffuse through the polyethylene bag and different contaminants diffuse at different rates.

The No Purge Sampler described in U.S. Pat. Nos. 6,837, 120 and 6,481,300 has overcome many of the problems associated with the sampling techniques described above. The No Purge Sampler is a sampling sleeve with a ballast. The sampling sleeve includes a check valve. While the sampling sleeve is lowered into a well, the check valve remains closed. Once the sampling sleeve is properly positioned in the well, a sample of the well can be taken by cycling the sleeve up and down. On the up stroke, the check valve allows fluid to enter the sampling sleeve. As the sampling sleeve is cycled down, the check valve closes. This cycle is repeated until the sleeve is full of fluid. Once the sampling sleeve is filled, the back pressure of the fluid in the sampling sleeve causes the check valve to remain closed thereby preventing additional fluid from entering the sampling sleeve as it is removed from the well.

While this design addresses many of the problems associated with other well sampling techniques, several issues remain. First, all no-purge passive sampling devices must stay immobile in the well for some period of time to allow the well to recover from mixing of the water column as the device is lowered into the well. This is known as the well equilibration period and may last from several days to several weeks. The sampling sleeve described in U.S. Pat. Nos. 6,837,120 and 6,481,300 results in much less mixing than competing devices, but still may require some well equilibration time depending on the well diameter, sampler diameter, permeability, etc.

In addition, the check valve described in U.S. Pat. Nos. 6,837,120 and 6,481,300, effectively prevents fluid from entering the sampling sleeve as it is removed from the well. However, on removal, fluid from the well can get trapped above the check valve. This extraneous fluid has the potential to contaminate the fluid sample in the sampling sleeve. This problem is compounded when sediment from the well collects above the check valve during the equilibration period.

Therefore, a need exists for an improved no purge sampling device that reduces mixing and drag-down during deployment and allows extraneous fluid to drain off the check valve during removal.

SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

U.S. Pat. Nos. 6,837,120 and 6,481,300 are herein incorporated by reference in their entirety, The present embodiments are an improvement to the inventions disclosed in U.S. Pat. Nos. 6,837,120 and 6,481,300 and much of the material in this application has been taken directly from those patents.

The disclosed embodiments relate to improved no purge samplers, which include at least one aperture formed in the flexible body above the check valve.

The present invention overcomes the aforementioned problems by providing a no purge "thief" or "grab" sampler which is disposable, inexpensive, and easy to operate. The no purge sampler of the present invention reduces equilibration time, reduces the chance of sample contamination, eliminates purge water, and minimizes labor costs associated with the sampling process.

The no purge sampler for collecting fluid samples, constructed according to the present invention, includes a tube having a sealed first end and a second end, the tube defining an interior cavity, a buoyancy-compensating ballast can be secured to the first end of the tube, and a check valve disposed at the second end of the tube. At least one aperture is formed above the check valve on the second end of the tube. The tube is preferably made of a flexible, pliant material.

To collect fluid samples, the no purge sampler is lowered into the fluid to be sampled. The buoyancy-compensating ballast allows the sampler to sink to a desired level. The apertures formed above the check valve on the second end of the tube modify the fluid flow pattern around the second end of the tube as it is lowered into the fluid, allowing it to slip downward through the fluid more smoothly, reducing drag-down and mixing, which significantly reduces the equilibration period. Once the sampler reaches the desired depth, the tube is filled. The apertures formed above the check valve promote fluid flow and prevent sediment or other contaminants from collecting on top of the check valve during the equilibration period.

The check valve is opened each time the sampler is pulled upwardly, allowing fluid to enter the interior cavity. The up and down motion is repeated until the interior cavity of the tube is fully expanded and filled with fluid. Once the interior cavity is filled, the pressure of the fluid in the tube causes the check valve to close, thereby preventing additional fluid from entering the interior cavity. The sampler is then pulled out of the fluid without losing any of the fluid in the interior cavity of the tube or allowing additional fluid to enter the sampler. The apertures above the check valve again promote fluid flow above the check valve thereby reducing sediment or other contaminates that may get trapped on the top of the check valve as the sampler is removed from the well.

In another embodiment, the up and down pumping method may be replaced with a single pull method for filling the interior cavity of the tube. In this embodiment, the sampler is lowered so that the second end of the sampler is aligned with the bottom of the sampling interval in the well. The sampler is then pulled through the sampling interval with a single pull such that the cavity is filled before the top of the sampling interval in the well. Once the cavity is full, the pressure of the fluid in the tube causes the check valve to close, thereby preventing additional fluid from entering the interior cavity. The sampler is then pulled out of the fluid without losing any of the fluid in the interior cavity of the tube or allowing additional fluid to enter the sampler. The apertures above the check valve again promote fluid flow above the check valve thereby reducing sediment or other contaminates that may get trapped on the top of the check valve as the sampler is removed from the well.

The check valve disposed within the sampler can be of any type, including, but not limited to, a floating ball-type check valve, collapsing reed valve, lift check valve, and the like. The check valve remains closed when the sampler is lowered into the fluid to be sampled. The check valve opens when the sampler is pulled upward and it is subjected to a fluid pressure differential across it and doses again on the downstroke. When the interior cavity of the tube is filled with the sampled fluid, the check valve remains closed, thereby preventing additional unwanted fluid from entering the cavity as the sampler is recovered from the well through the overlying water column.

The no purge sampler can be made of any diameter or length to accommodate a desired sample volume or well size. The no purge sampler may be constructed from any pliant material depending on the application. The dimensions of the sampler are dependent on the application in which it is utilized. Although the no purge sampler of this invention is preferably used to collect groundwater samples from discrete intervals within wells, it could also be used to sample fluid from streams, oceans, lakes, storage tanks, or any other fluid bearing medium.

No purge samplers of the present invention require a simple operating procedure. Unlike previously known sampling devices, there is no need for extensive training of field personnel to utilize the no purge sampler of the present invention. Moreover, no purge samplers of the present invention are inexpensive to produce and do not require costly equipment to operate. Unlike the diffusion sampler described above, no purge samplers of this invention have broad applicability and are not limited to the sampling of fluids containing specific types of contaminants. Finally, the no purge sampler disclosed herein reduces equilibration time and reduces the chances of sample contamination.

This invention, together with the additional features and advantages thereof, which was only summarized in the foregoing passages, will become more apparent to those of skill in the art upon reading the description of the preferred embodiments, which follows in the specification, taken together with the following drawings.

BRIEF DESCRIPTION OF THE FIGURES

The accompanying figures, in which like reference numerals refer to identical or functionally-similar elements throughout the separate views and which are incorporated in, and form a part of, the specification, further illustrate the embodiments and, together with the detailed description, serve to explain the embodiments disclosed herein.

DETAILED DESCRIPTION

U.S. Pat. Nos. 6,837,120 and 6,481,300 are herein incorporated by reference in their entirety. The present embodiments are an improvement to the inventions disclosed in U.S. Pat. Nos. 6,837,120 and 6,481,300 and much of the material in this application has been taken directly from those patents.

The particular values and configurations discussed in these non-limiting examples can be varied and are cited merely to illustrate at least one embodiment and are not intended to limit the scope thereof. The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The terminology used herein is for the purpose of describing particular embodiments only and is not intended to be limiting of the invention. As used herein, the singular forms "a", "an", and "the" are intended to include the plural forms as well, unless the context clearly indicates otherwise. As used herein, the term "and/or" includes any and all combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
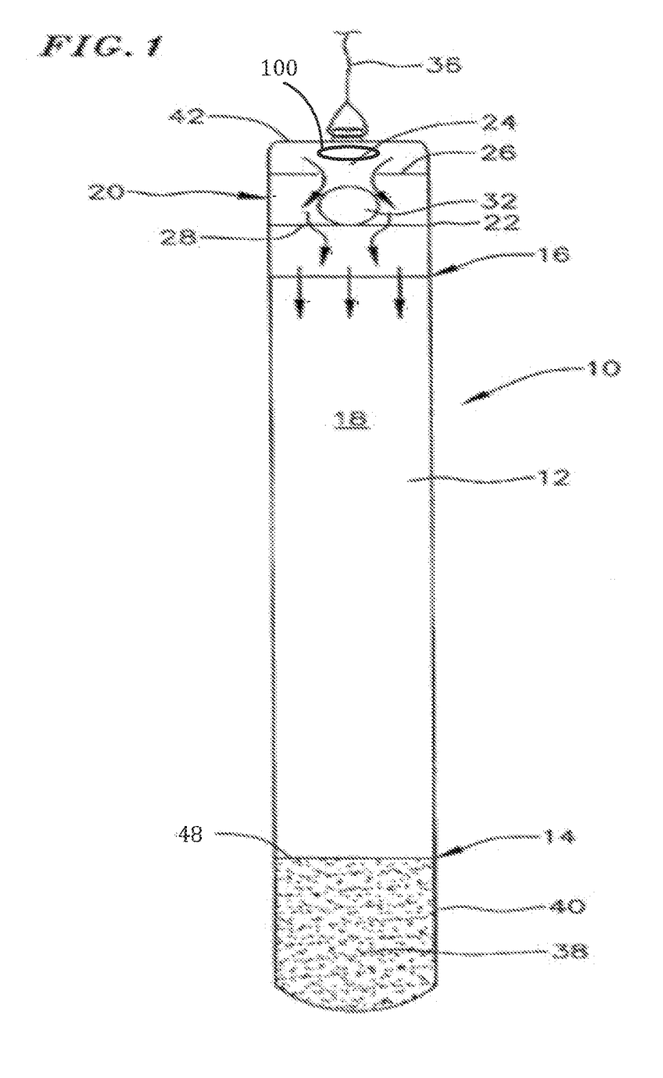
FIG. 1 is a schematic cross-sectional side view illustrating one embodiment of the present invention.
Figure 2:
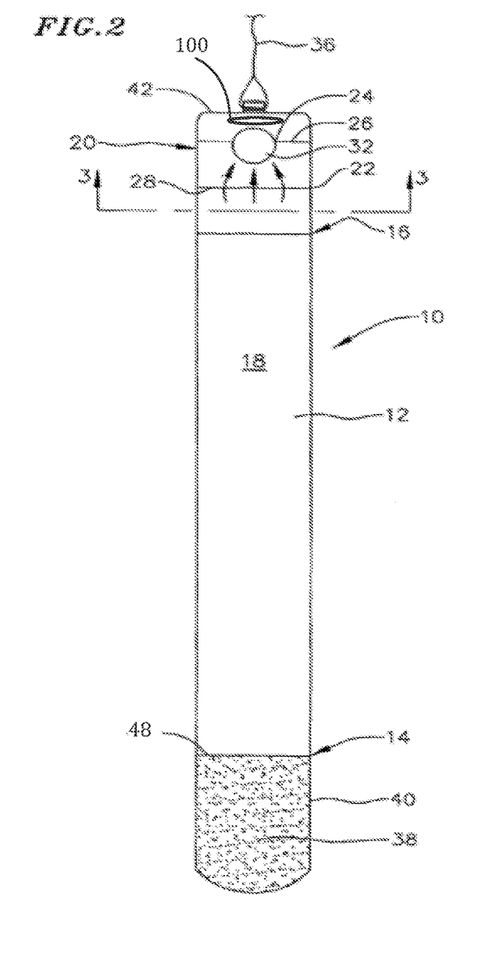
FIG. 2 is a schematic cross-sectional side view of the invention of FIG. 1, wherein the interior cavity of the tube has been filled with a sample fluid and the check valve is shown in a closed position, preventing further fluid from entering the interior cavity of the tube.

Referring to FIGS. 1 and 2, the no purge sampler 10 of the present invention includes a flexible tube 12 having a first end 14 and a second end 16. In the illustrated embodiment, the first end 14 is disposed below the second end 16 when the sampler 10 is held in a vertical position, as shown in FIGS. 1 and 2, The tube 12 is preferably constructed of a flexible polymeric material sheet or film, e.g., polyethylene, and defines an interior cavity 18 for collecting fluid samples therein. In a preferred embodiment of the present invention, the tube 12 has a thickness of approximately 4 mils (or 4/1000 of an inch). The material used to construct tube 12 is preferably transparent to allow visual inspection of the collected sample. The first end 14 of tube 12 is sealed and the second end 16 is open providing an access or pathway for the sample being collected to enter the interior cavity 18 of the tube.

In another preferred embodiment, tube 12 is formed of one or more durable polymeric sheets that are approximately 4 mils thick. The tube 12 is formed by heat sealing, or otherwise bonding the edges of two sheets of polymeric material together to form a tube 12 that can lay flat when it is not filled, and is cylindrical in shape when it is filled.

Figure 3:
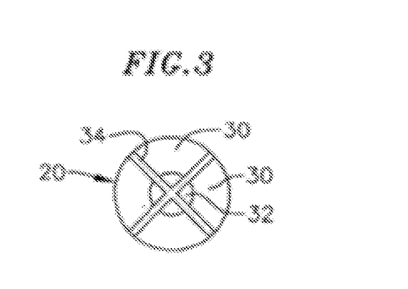
FIG. 3 is a cross-sectional end view of the check valve of the present invention taken along line 3 of FIG. 2.

The sample fluid enters the cavity 18 through a check valve disposed on the second end 16 of tube 12. In one embodiment, the check valve is a floating ball type check valve 20, as shown in FIGS. 1 and 2. In another embodiment, the check valve is a collapsing reed valve as shown in FIGS. 8A-F. In the embodiment illustrated in FIGS. 1 and 2, the outer edge 22 of check valve 20 is sealably connected around the inside surface of the tube's second end 16 to thereby prevent any fluid from flowing into the interior cavity 18 around the check valve's outer edge. The check valve 20 has a first plateau 26 and a second plateau 28 preferably positioned beneath the first plateau. In a preferred embodiment, the first plateau is ring-shaped with an inlet opening 24 in its center through which the collected fluid first enters the sampler. The second plateau 28 is also preferably ring-shaped and includes a plurality of openings 30, as shown in FIG. 3, that lo the collected fluid entering the sampler to flow into the interior cavity 18 of tube 12.

A check ball 32 is confined between the first and second plateaus 26 and 28. The width of the inlet opening 24 of the first plateau 26 is dimensioned to be less than the diameter of the check ball 32 such that when the check ball is pressed up against the inlet opening 24 under an exerted force, the inlet opening is closed and no fluid is permitted to enter the interior cavity. Furthermore, the inlet opening 24 prevents the check ball 32 from exiting the sampler 10 since the diameter of the check ball is too large to fit through the inlet opening 24. The second plateau 28 includes barrier members 34, best shown in FIG. 3, that prevent check ball 32 from entering the interior cavity 18 of tube 12. FIG. 1 illustrates the check ball 32 in a position adjacent to the second plateau 28. When the check ball 32 is in this position, the inlet opening 24 is open allowing sample fluid to enter the check valve 20.

At least one, and preferably two or more apertures 100 are formed through the sides of the tube 12 above the check valve 20, and more specifically above plateau 26. Apertures 100 serve multiple purposes. First, the apertures 100 alter the fluid dynamics of the fluid flow surrounding the sampler 10 as it is lowered into a well. The apertures 100 streamline the sampler 10. The change in fluid dynamics results in significantly less mixing and drag-down as the sampler 10 is moved into position in the well. In dye tests, apertures 100 have proven to reduce drag-down by approximately 75%. As a result, samplers 10 with apertures 100 require little or no equilibration time.

In a preferred embodiment, a sampler 10 with apertures 100 can be deployed in a well, filled, and recovered immediately because apertures 100 drastically reduce drag-down. Immediate recovery of the sampler 10 eliminates the need for follow up trips by a technician to recover the sampler 10 after an equilibration period.

Testing indicates that eliminating the equilibration period lowers the turbidity of collected samples by preventing the accumulation of sediment on top of the check valve which sometimes occurs when the sampler 10 is left in a well for an extended period of time. Upon removal of the sampler 10 from the well, apertures 100 allow fluid flow through tube 12 above check valve 20. This fluid flow tends to reduce the amount of sediment or other contaminates that collect above check valve 20 in sampler 10.

In addition, the apertures 100 allow fluid that would otherwise collect on the check valve to drain away from the valve when the sampler 10 is recovered from a well, reducing the chance that extraneous fluid might enter the sampler 10. Consequently, apertures 100 improve sampler 10 by reducing fluid sample contamination.

FIG. 2 illustrates the check ball 32 blocking the inlet opening 24 thereby preventing fluid from entering the valve. The check valve 20, including the check ball 32, is preferably made of a material that is resistant to corrosion caused by the contaminants that may be found in the sample fluid. For example, the check valve and ball may be made of various plastics, such as polypropylene, polyethylene, impact polystyrene, or ABS or the like. The check ball has a density less than the density of the fluid being sampled. The check ball floats such that it is seated in the opening 24 when the sampler is full.

In operation, the no purge sampler 10 is guided into the fluid from which a sample is desired. A suspension line 36 and ballast 38 can be used to assist with the submersion of the sampler 10 in the fluid. In one embodiment, the suspension line 36 is connected to a submersion handle 42 mounted on the top of the sampler. In a preferred embodiment, a buoyancy-compensating ballast compartment 40 is secured to the first end 14 of tube 12. The buoyancy-compensating ballast compartment 40 is filled with an appropriate ballast 38 to allow the sampler to sink to a desired level. One type of ballast that can be used is an inexpensive sand that is free from contaminants and soluble salts. In a preferred embodiment, the ballast is a steel weight, preferably triple sealed to protect against corrosion and interference with the sample water. The ballast is preferably isolated from the sample tube 12 by the ballast compartment 40. In one embodiment, the ballast is installed in the bottom end of the tube 12 and a heat seal 48 is formed in the tube to define the top of the ballast compartment. In another embodiment, the ballast compartment 40 is detachable from tube 12 and can be reused with other samplers.

Figure 4A:
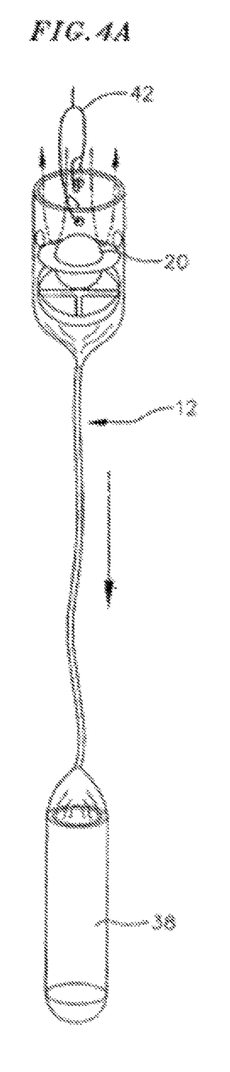
FIGS. 4A through 4C illustrate the operation of the sampler of the present invention.
Figure 4B:
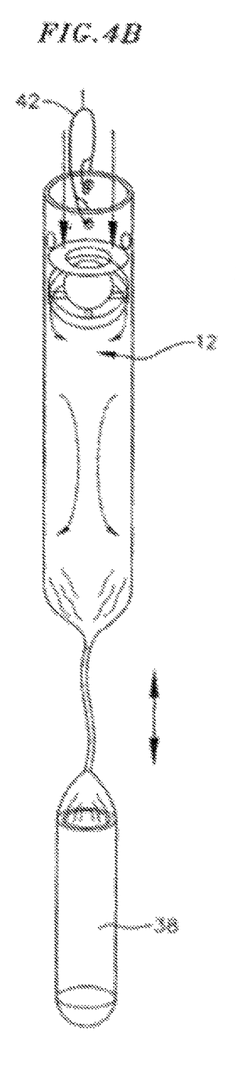
Figure 4C:
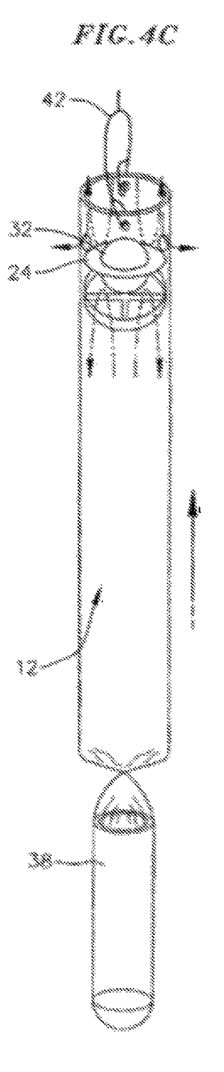

The operation of one embodiment of the sampler for collecting a sample of ground water from a monitoring well is best shown in FIGS. 4A through 4C. To collect the ground water sample, the no purge sampler 10 is lowered into the fluid in the well being sampled. As the sampler is lowered into the well, the check valve 20 remains closed and hydrostatic pressure collapses the flexible tube 12, as shown in FIG. 4A.

In a preferred embodiment, the check valve 20 is a collapsing reed valve. In this embodiment, apertures 100 are formed above the check valve. As the sampler 10 is lowered into the well, the sampler 10 and the check valve 20 remain collapsed and flat. The collapsed sampler 10 is streamlined by the apertures 100. The additional streamlining from apertures 100 and the slim profile of the collapsed sampler 10 and check valve 20 minimize mixing of water within the well. During the submersion phase of the sampling operation, the check valve 20 prevents fluid flow into the sampler 10. Because the drag-down and mixing are minimal, a sample can be collected immediately.

During the sampling phase of the operation, the sampler 10 is moved up and down in the screened section of the well to pump water into the flexible tube 12. The check valve 20 opens each time the sampler 10 is pulled upwards allowing water to enter the interior cavity 18 via the opening 24. The up and down motion is repeated until the interior cavity 18 of the tube is filled with water. In the preferred embodiment, the sampler 10 is manually raised and lowered about 6 inches using the suspension line 36. The cycle is preferably repeated a minimum of 20 times. On the upstroke, the upper check valve 20 opens and water moves into the tube 12, expanding it, as shown in FIG. 4B. During the down cycle, the check valve 20 closes trapping the sample in the tube 12. The next upstroke repeats the process, which continues until the tube 12 is full.

The flexible tube 12 preferably has a degree of elasticity such that when the tube 12 is full, the tube 12 exerts pressure on the fluid in an attempt to return to its original volume. The pressure of the water in the tube 12 causes the check valve 20 to remain closed, as shown in FIG. 4C, thereby preventing additional water from entering the cavity 18. The check valve 20 floats such that it stays seated when the tube 12 is full. The sampler 10 is then pulled out of the screened section of the well without losing any of the sample water in the tube 12 and without allowing extraneous water into the sampler 10 during recovery.

Figure 5:
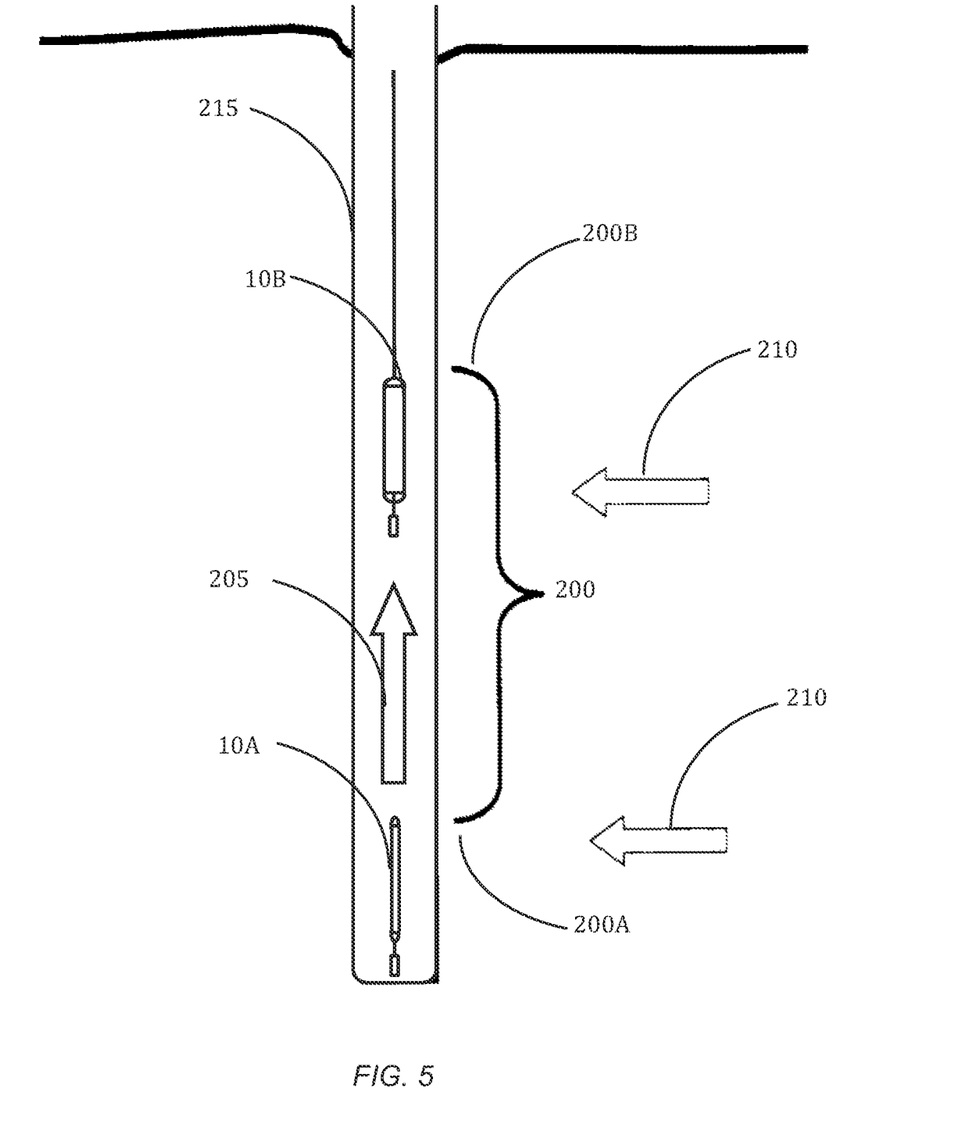
FIG. 5 illustrates an alternative operation of the sampler of the present invention.

An alternative sampling phase is illustrated in FIG. 5. In this embodiment of the sampling phase of the operation, the sampler 10 is first deployed in the well 215. The unfilled sampler 10A can be lowered so that the second end of the unfilled sampler 10A aligns with the bottom 200A of the sampling interval 200. Fluid may move through and around the sampling interval 200 and well 215 as illustrated by arrows 210. Once the unfilled sampler 10A is in position at the bottom 200A of the sampling interval 200, it can be drawn upwards through the sampling interval 200. On the upstroke, the check valve 20 opens and fluid moves into the tube 12, expanding it, as shown in FIG. 6B. The sampler 10 fills with fluid before reaching the top of the sampling interval 200B. Once the sampler 10B is full, the pressure of the fluid in the tube 12 causes the check valve 20 to remain closed.

Figure 6A:
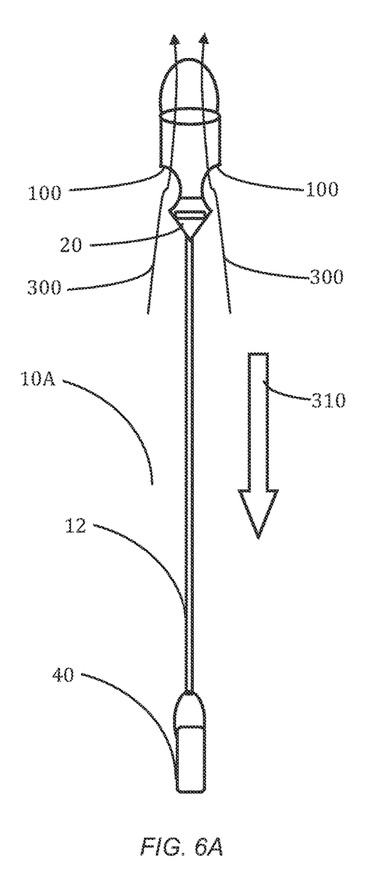
FIGS. 6A through 6B illustrate an alternative operation of the sampler of the present invention.
Figure 6B:
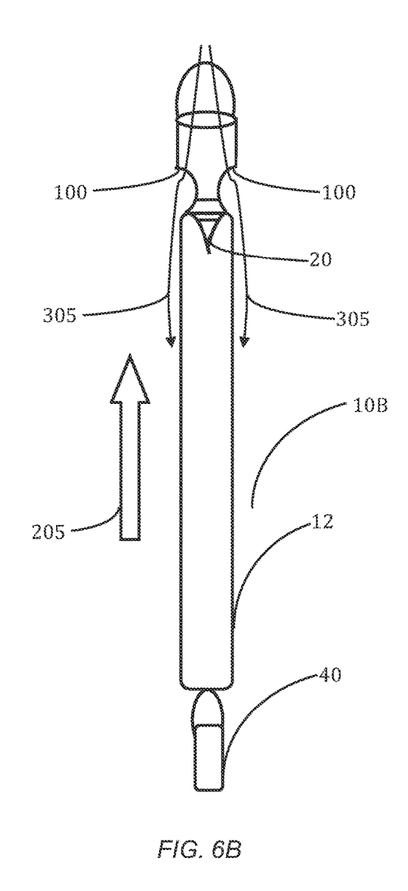

The single pull sampling phase is further illustrated in FIGS. 6A and 6B. In FIG. 6A, the unfilled sampler 10A is shown being deployed as illustrated by arrow 310. Here the ballast compartment 40 serves to pull the unfilled sampler 10A down through the fluid in the well. Apertures 100 located above check valve 20 improve the fluid dynamics of unfilled sampler 10A as it is deployed. Arrows 300 illustrates the fluid path around and through apertures 300.

As shown in FIG. 6B, after the unfilled sampler is properly placed it can be pulled upward through the sampling region 200 as shown by arrow 205, The check valve 20 allows fluid to enter the tube 12 until it is filled. Once the sampler 10B is filled, the check valve prevents any further fluid from entering. As the filled sampler 10B is drawn upward, apertures 100 allow fluid to flow down through the top of the filled sampler 10B and out the apertures 100 as shown by arrows 305. This prevents contaminates from collecting on the top of the check valve as the filled sampler 10B is removed from the well.

Figure 7:
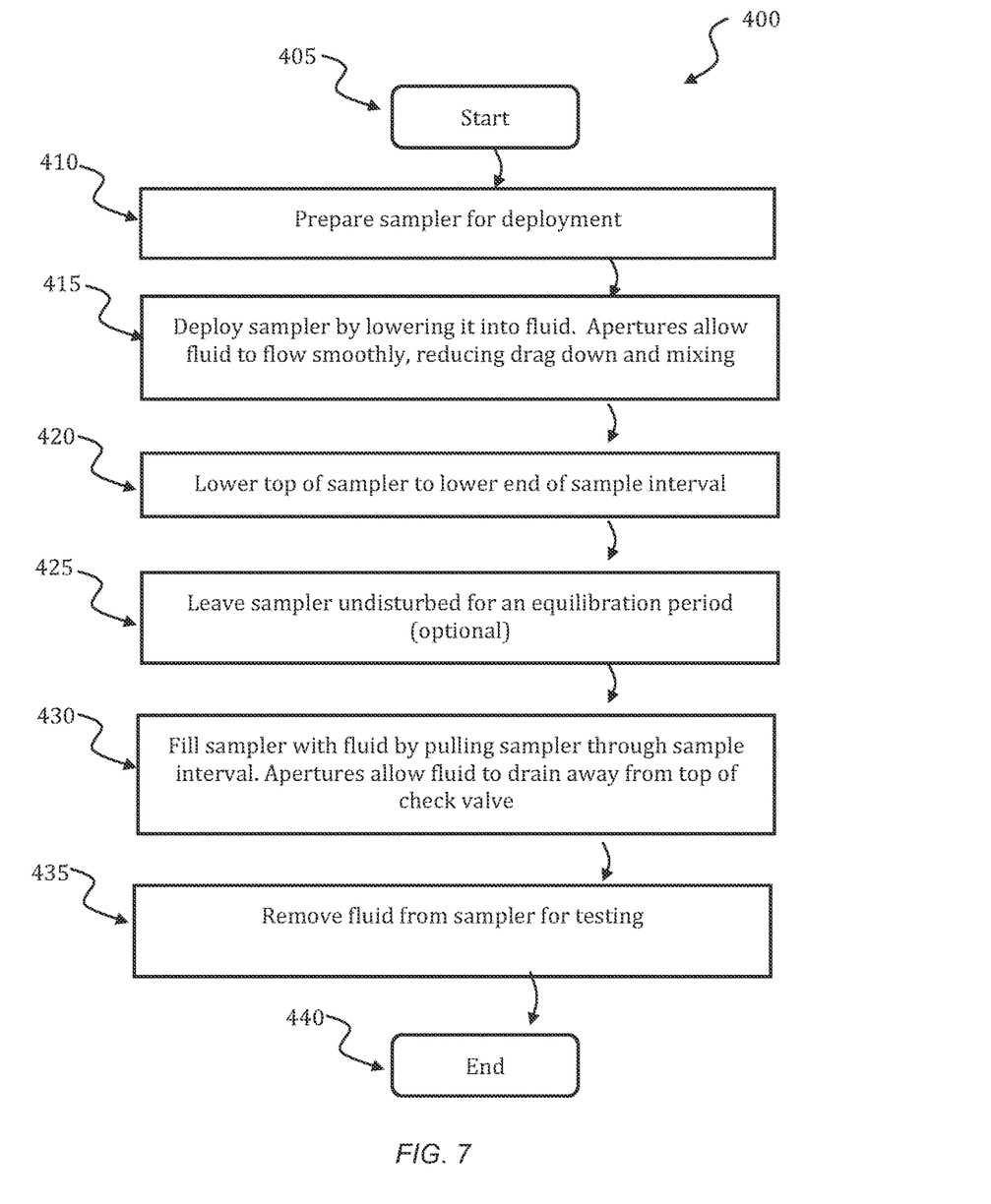
FIG. 7 illustrates logical operational steps associated with a method for sampling a fluid in accordance with an embodiment of the present invention.

The method for single pull sampling 400 is illustrated in FIG. 7. The method begins at step 405. At step 410, a sampler can be prepared for deployment. This step may include selecting the appropriate sized sampler for the desired application, selecting the appropriate ballast for the desired application, and selecting the appropriate number, type and arrangement of apertures for the desired application.

Next at step 415, the sampler is deployed into the fluid as shown in FIG. 6A. The sampler is lowered so that the second end of the sampler is roughly level with the lower end of the sampling interval, as shown at step 420. Optionally, at step 425 the sampler may be left undisturbed for well equilibration depending on the specific application. It will commonly be the case that step 425 is unnecessary because the apertures sufficiently reduce drag-down and mixing.

At step 430, the sampler is drawn up though the sampling interval. In a single upward stroke, the sampler can be filled with fluid from the sampling interval. The check valve prevents any further fluid from entering the sampler once it is filled. The sampler can now be removed from the fluid at step 435 so that the captured fluid can be tested in accordance with the desired application. The method ends at step 440.

Check valves used in the present invention can be of any type, including, but not limited to, a floating ball-type check valve 22 (as shown in FIGS. 1-3), collapsing reed valves 115 (as shown in FIGS. 8A-F), flapper valves, lift check valves, and the like. The check valve 20 must remain closed when being submerged into the fluid to be sampled. The check valve 20 must then be opened when it is pulled upward and closed again on the downstroke. When the interior cavity 18 of the tube 12 is filled with the sampled fluid, the check valve 20 remains closed, thereby preventing additional fluid from entering the cavity 18 and allowing the sampler 10 to be removed from the fluid to be sampled without losing any of the fluid in the interior cavity 18 itself. The check valve 20 can be dome-shaped for better water drainage.

Figure 8A:
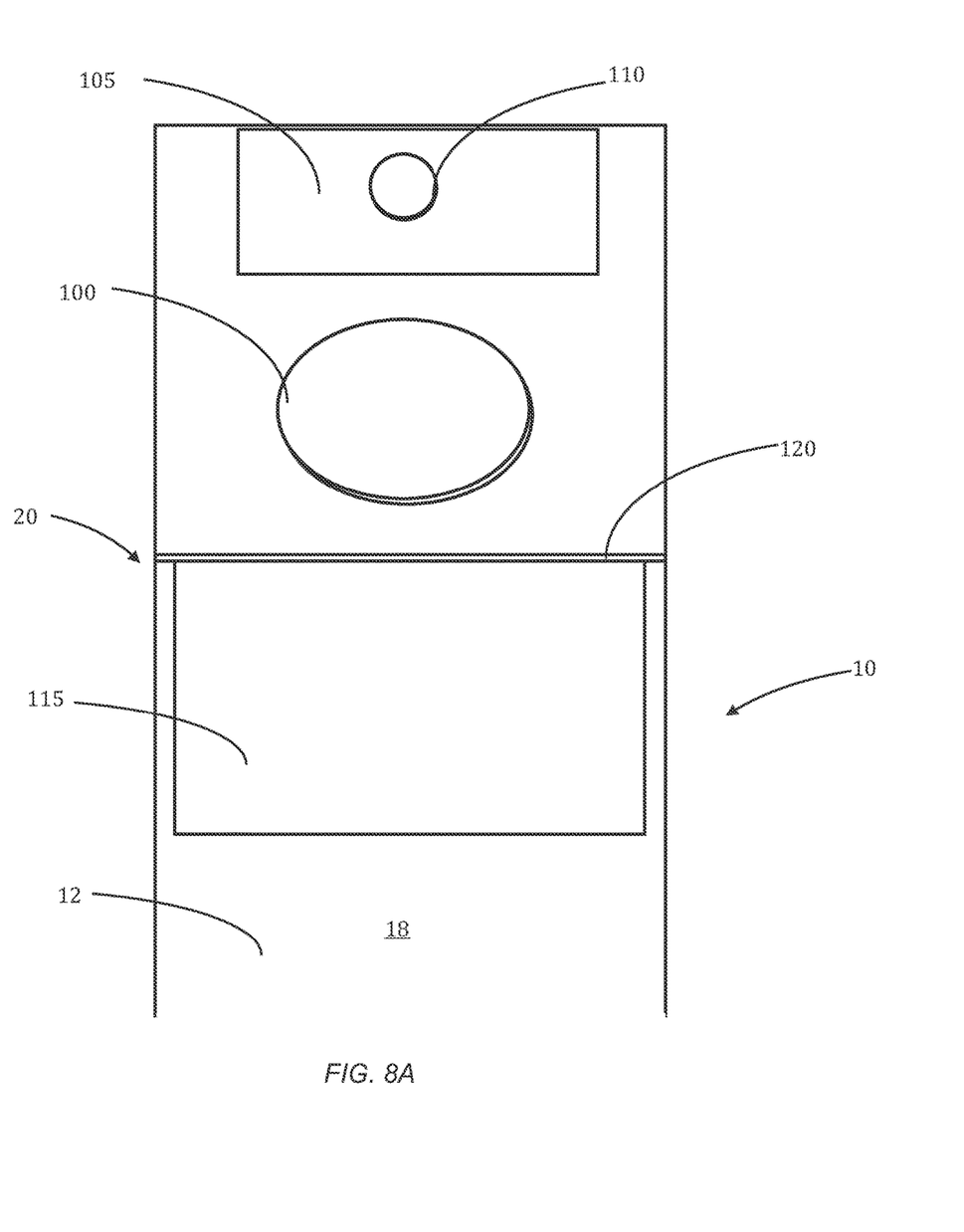
FIGS. 8A through 8F are cross-sectional views of alternative embodiments of the aperture above the check valve in accordance with the disclosed embodiments.

FIGS. 8A-8F illustrate alterative embodiments of apertures 100. In FIG. 8A, apertures 100 are illustrated as circular in shape. It should be appreciated that any number of apertures may be provided on tube 12 above check valve 20. In FIG. 8A, two apertures 100 are shown. The apertures 100 are configured on tube 12 such that when the sampler 20 is empty and lying flat, the apertures 100 align to form a hole through tube 12. In other embodiments, any number of apertures 100 may be formed on tube 12 and may align, partially align, or may not align.

Tube 12 may include at least one stiffening member 105 and preferably two stiffening members formed of a hard plastic or other such material Stiffening members 105 can be located above apertures 100. The stiffening members 105 include at least one hole 110, which penetrates both the stiffening member 105 and tube 12. Submersion handle 42 can be operably connected with or through holes 110 for recovery of sampler 10. The stiffening member 105 lends support to tube 12 upon recovery because the force experienced by the tube as it is pulled through fluid may be sufficient to rip through the thin material from which the tube 12 is formed.

In FIGS. 8A-8F, sampler 10 is also shown with a check valve 20 comprising a collapsing reed valve 115. Collapsing reed valve 115 is preferably used in embodiments with apertures 100 because the collapsing reed valve 115 allows sampler 10 to maintain a flat profile as it is lowered into the well. The collapsing reed valve 115 includes at least one reed binding member 120 which fastens collapsing reed valve 115 to the inside of tube 12. Reed binding member 120 must seal the portion of tube 12 above the check valve 20 from the potion below the check valve 20 in order for the sampler 10 to operate properly.

Figure 8B:
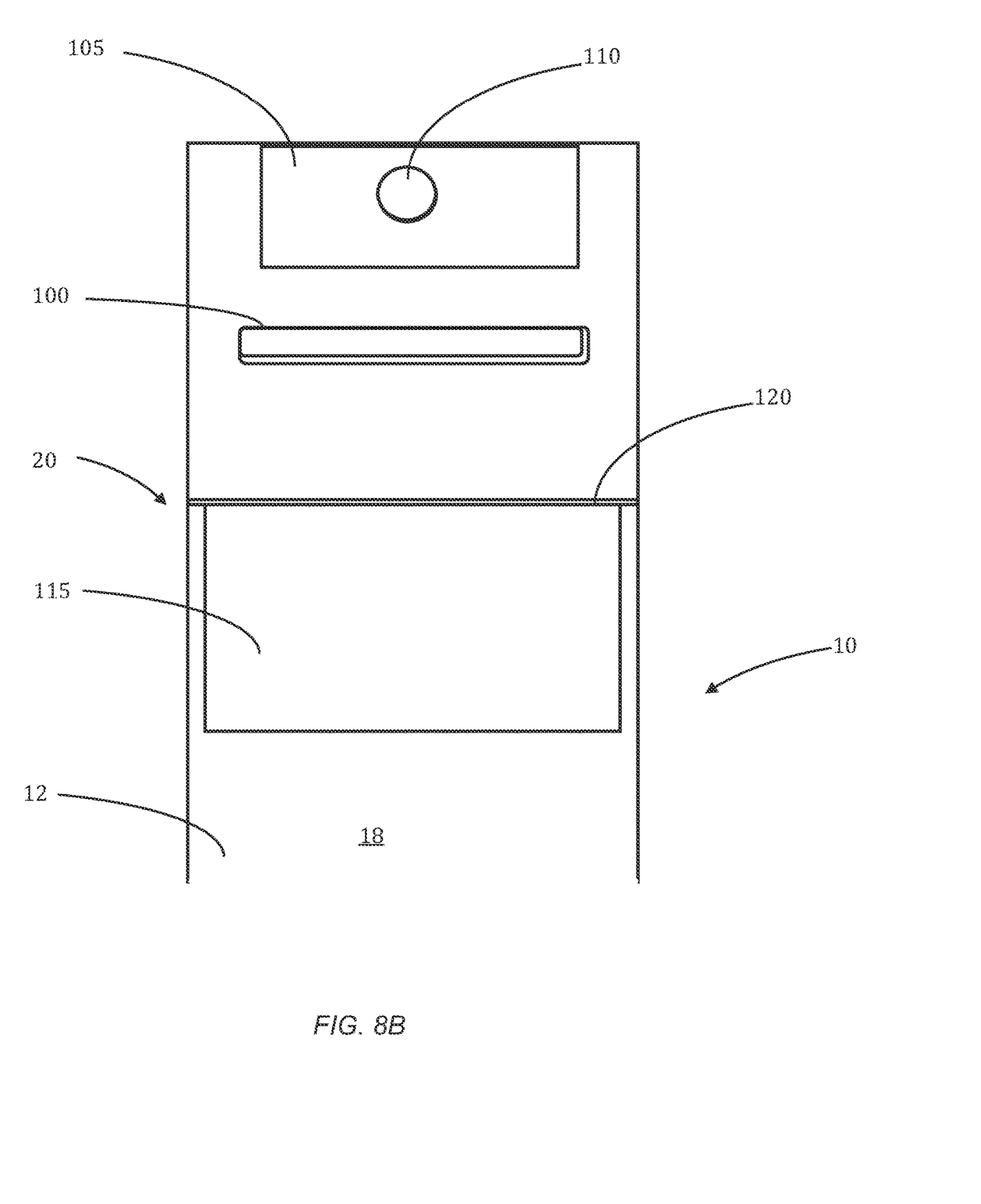
Figure 8C:
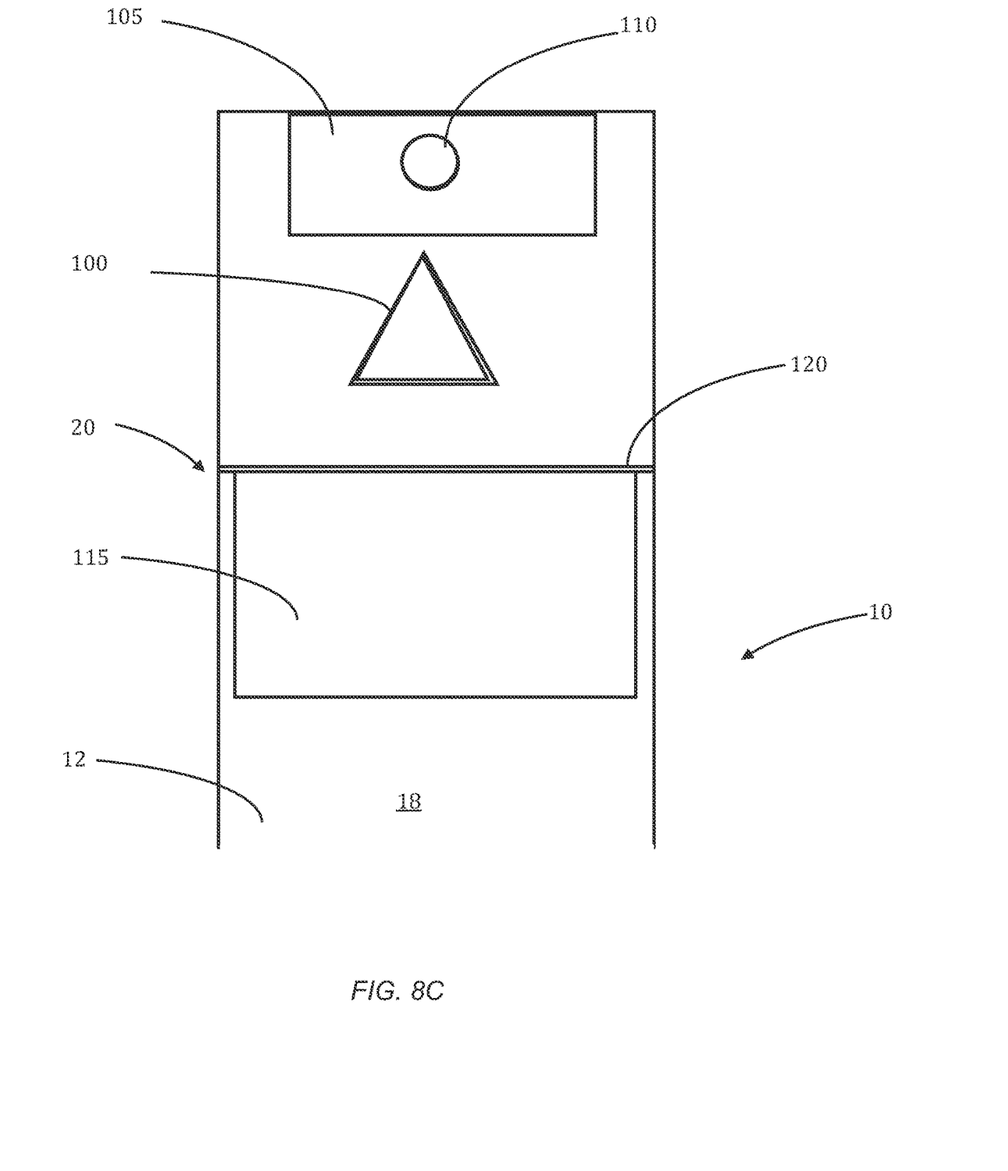
Figure 8D:
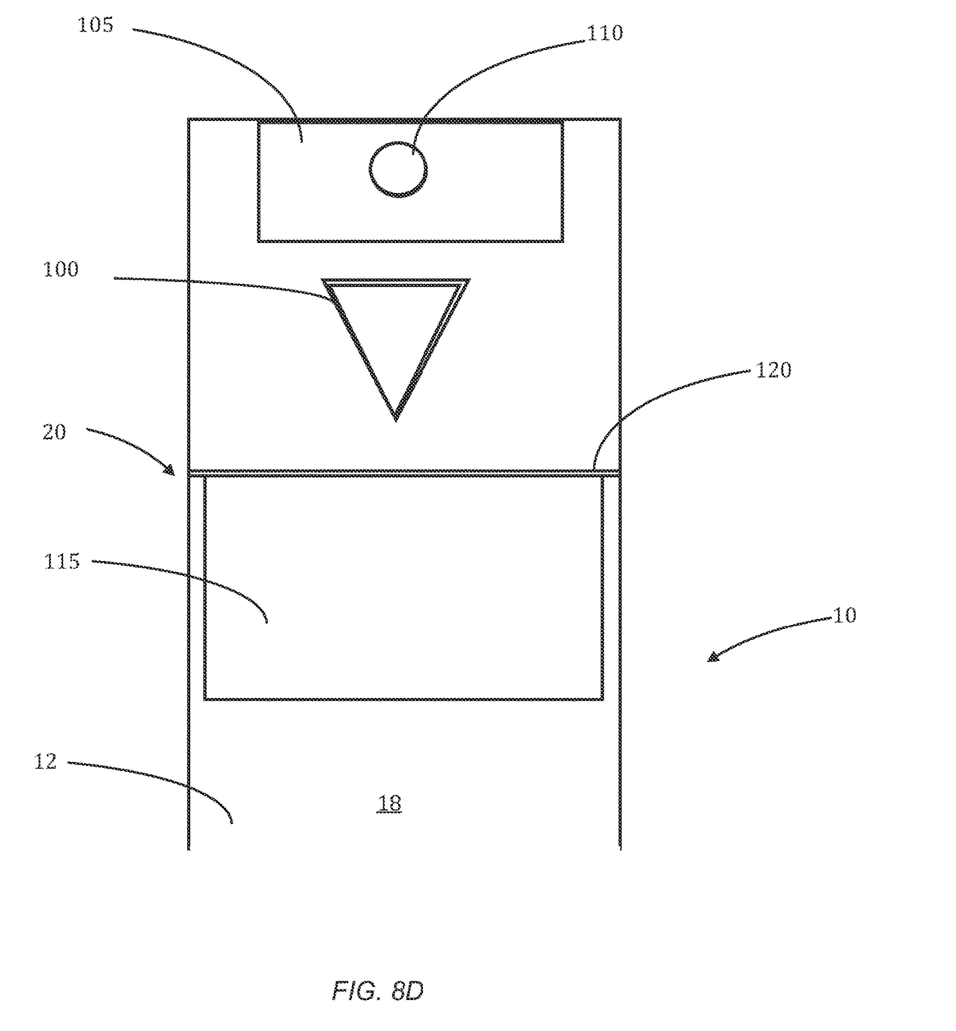
Figure 8E:
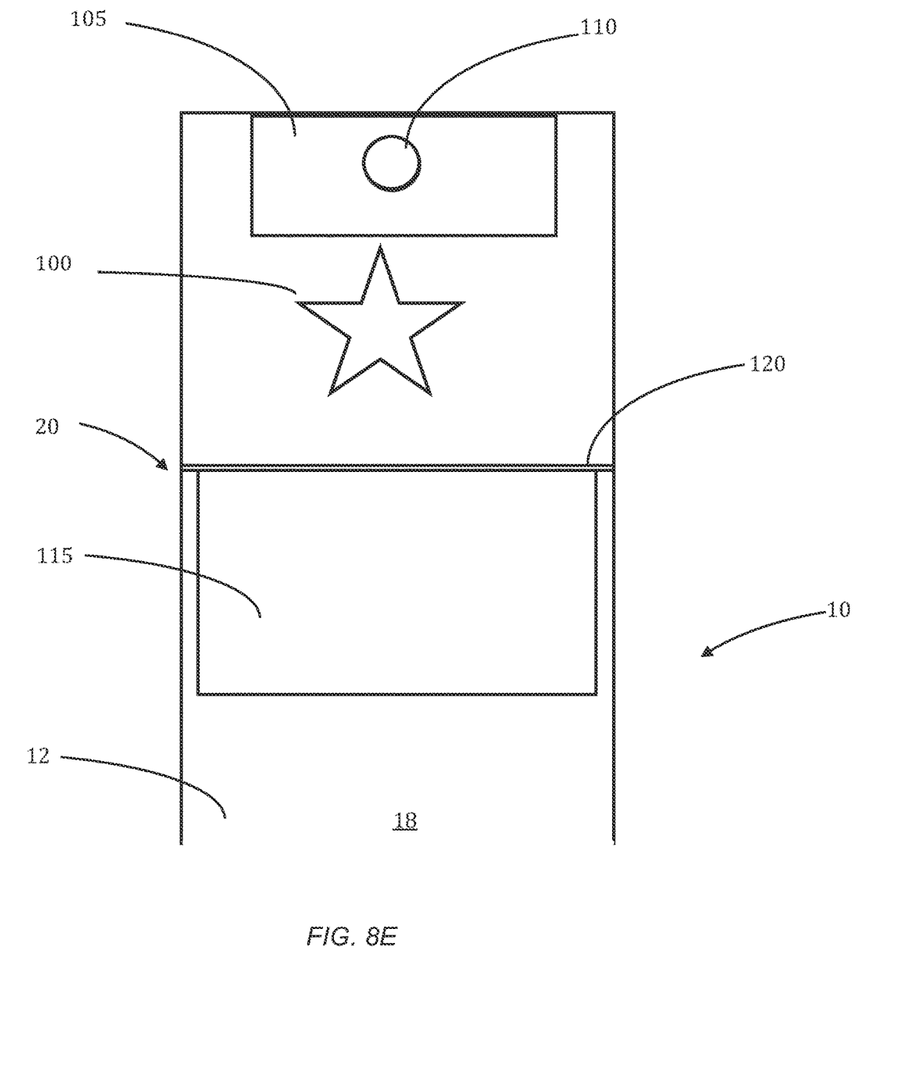
Figure 8F:
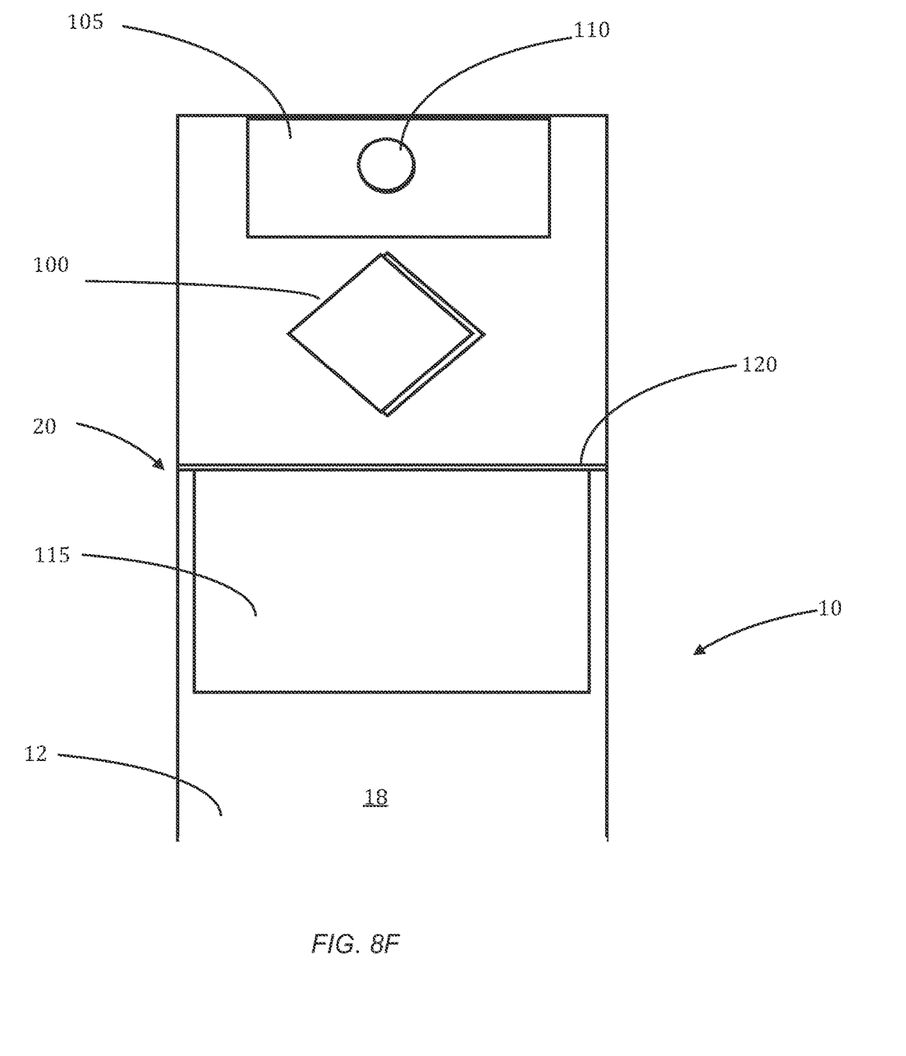

FIG. 8B illustrates an alternative embodiment wherein apertures 100 are shaped as slits in tube 12. In other embodiments, the apertures 100 may be triangles (FIG. 8C), inverted triangles (FIG. 8D), star shaped (FIG. 8E), or diamond/square shaped (FIG. 8F). The specific shape of apertures 100, the number of apertures 100, the alignment of apertures, and the fluid itself will all affect the fluid dynamics of the sampler 10 as it is lowered into the well. Therefore, different embodiments of apertures 100 may be preferred in different applications and may be selected to minimize drag-down and mixing. It should be appreciated that other shapes may alternatively be used as apertures 100 without departing from the scope of this disclosure.

The samplers of the present invention can be made of any diameter or length to accommodate a desired sample volume or well size. Apertures 100 may similarly be of any size, but preferably range between 1 and 5 inches in diameter. The dimensions of the sampler and the apertures 100 are application dependent. Although the no purge samplers described herein are preferably used to collect groundwater samples from discrete intervals within wells, they can also be used to sample fluids from streams, oceans, lakes, storage tanks or any other fluid bearing medium.

As described above, the operating procedure of the no purge sampler 10 of the present invention is simple. Unlike previously known sampling devices, there is no equilibration period required with the no purge sampler described herein, Moreover, the no purge sampler of the present invention is inexpensive to produce and does not require costly equipment to operate. The sampler is disposable, thus eliminating errors resulting from contaminants that may remain in the sampler from previous sampling events. The low cost of the samplers will deter covert reuse of disposable samplers. Finally, unlike the diffusion sampler described above, the no purge sampler 10 has broad applicability and is not limited to the sampling of fluids containing specific types of contaminants.

It is to be understood that various modifications can be made to the disclosed embodiments of the present invention without departing from the spirit and scope thereof. For example, various sizes of the no purge sampler and particularly, various tubing diameters, and aperture diameters are contemplated as well as various types of valve, tube, and ballast materials and components. Various sizes, shapes, alignments, and arrangements of apertures are further contemplated. Also, various modifications may be made to the configuration of the parts and their interaction. Therefore, the above description should not be construed as limiting the invention, but merely as an exemplification of preferred embodiments thereof. Those of skill in the art will envision other modifications within the scope and spirit of the present invention as defined by the appended claims.

Based on the foregoing, it can be appreciated that a number of different embodiments, preferred and alternative are disclosed herein. For example, in one embodiment, a sampling device for obtaining a sample of fluid from a fluid body is disclosed, the sampling device comprising a tube which comprises a pliant material having a sealed first end and a second end, the tube defining an interior cavity. A check valve is disposed at the second end of the tube; the check valve is adapted to permit inflow of fluid through the valve and into the interior cavity when the sampling device is being pulled upwardly in the fluid body, and to reversibly constrict outflow of collected fluid by closing the check valve when the sampling device is being lowered into the fluid body. The check valve remains closed as the sampling device is lowered into the fluid to be sampled, wherein the check valve opens when the sampling device is pulled upwards, and wherein the check valve remains closed when the interior cavity is filled with the fluid. At least one aperture is disposed past the check valve at the second end of the tube, wherein the aperture is adapted to streamline the tube and allow fluid to flow through the tube above the check valve.

In other embodiments, the check valve comprises a collapsing reed valve. The tube comprises two pieces of the pliant material sealed together, wherein the tube remains flat when it is unfilled. The at least one aperture is shaped as at least one of an oval, a square, a triangle, an inverted triangle, a slit, a star, and a diamond.

In further embodiments, the sampling device includes the at least one aperture comprised as two or more apertures wherein the two or more apertures align, the two or more apertures partially-align, or the two or more apertures do not align.

It will be appreciated that variations of the above-disclosed and other features and functions, or alternatives thereof, may be desirably combined into many other different systems or applications. Furthermore, various presently unforeseen or unanticipated alternatives, modifications, variations or improvements therein may be subsequently made by those skilled in the art which are also intended to be encompassed by the following claims.

What is claimed is:

1. A sampling device for obtaining a sample of fluid from a fluid body, the sampling device comprising:
    a tube which comprises a pliant material having a sealed first end and a second end, the tube defining an interior cavity wherein the tube comprises two pieces of the pliant material sealed together thereby remaining flat when it is unfilled;
    a check valve disposed at the second end of the tube, the check valve adapted to permit inflow of fluid through the valve and into the interior cavity when the sampling device is being pulled upwardly in the fluid body, and to reversibly constrict outflow of collected fluid by closing the check valve when the sampling device is being lowered into the fluid body;
    wherein the check valve remains closed as the sampling device is lowered into the fluid to be sampled, wherein the check valve opens when the sampling device is pulled upwards, and wherein the check valve remains closed when the interior cavity is filled with the fluid; and
    two or more apertures disposed past the check valve at the second end of the tube wherein the two or more apertures partially align and, the two or more apertures are adapted to streamline the tube and allow fluid to flow through the tube above the check valve.

2. The sampling device of claim 1 wherein the check valve comprises a collapsing reed valve.

3. The sampling device of claim wherein one of the two or more apertures is shaped as at least one of:
    an oval;
    a square;
    a triangle;
    an inverted triangle;
    a slit;
    a star; and
    a diamond.

4. The sampling device of claim 1 wherein the two or more apertures do not align.

* * * * *